United States Patent
Szeifert et al.

(10) Patent No.: US 9,249,075 B2
(45) Date of Patent: Feb. 2, 2016

(54) PROCESS FOR PRODUCING POROUS OR FINELY DIVIDED SOLID INORGANIC MATERIALS

(71) Applicant: BASF SE, Ludwigshafen (DE)

(72) Inventors: Johann Martin Szeifert, Mannheim (DE); Michael Kutschera, Neustadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/172,122

(22) Filed: Feb. 4, 2014

(65) Prior Publication Data

US 2014/0221699 A1 Aug. 7, 2014

Related U.S. Application Data

(60) Provisional application No. 61/760,679, filed on Feb. 5, 2013.

(51) Int. Cl.
| | |
|---|---|
| *C07C 29/32* | (2006.01) |
| *C01B 33/154* | (2006.01) |
| *C01B 33/155* | (2006.01) |
| *C01B 33/158* | (2006.01) |

(52) U.S. Cl.
CPC .............. *C07C 29/32* (2013.01); *C01B 33/154* (2013.01); *C01B 33/155* (2013.01); *C01B 33/158* (2013.01)

(58) Field of Classification Search
None
See application file for complete search history.

(56) References Cited

U.S. PATENT DOCUMENTS

| | | | |
|---|---|---|---|
| 2,249,767 A | 7/1941 | Kistler | |
| 4,667,417 A | 5/1987 | Graser et al. | |
| 5,738,801 A | 4/1998 | Ziegler et al. | |
| 6,017,505 A * | 1/2000 | Ziegler et al. | ........... 423/338 |
| 6,129,949 A | 10/2000 | Schwertfeger et al. | |
| 6,516,537 B1 | 2/2003 | Teich et al. | |
| 2007/0003463 A1 | 1/2007 | Ajiri | |
| 2007/0134437 A1 | 6/2007 | Kin et al. | |
| 2007/0166226 A1 | 7/2007 | Holmes et al. | |

FOREIGN PATENT DOCUMENTS

| | | |
|---|---|---|
| DE | 195 41 992 A1 | 5/1997 |
| DE | 198 10 565 A1 | 9/1999 |
| EP | 0171722 A2 | 2/1986 |
| EP | 0 65 3377 A1 | 5/1995 |
| JP | 2007 099607 A | 4/2007 |
| JP | 2009 107857 A | 5/2009 |
| KR | 2012 0115068 A | 10/2012 |
| WO | WO-95/06617 A1 | 3/1995 |
| WO | WO-01/52981 A1 | 7/2001 |
| WO | WO-03/034979 A2 | 5/2003 |
| WO | WO-2005/100452 A1 | 10/2005 |
| WO | WO-2010/122049 A1 | 10/2010 |

OTHER PUBLICATIONS

U.S. Appl. No. 61/760,678, filed Feb. 5, 2013, Kutschera, M.
U.S. Appl. No. 61/760,677, filed Feb. 5, 2013, Szeifert, J.
U.S. Appl. No. 61/760,679, filed Feb. 5, 2013, Szeifert, J.

* cited by examiner

*Primary Examiner* — Yong Chu
*Assistant Examiner* — Ana Z Muresan
(74) *Attorney, Agent, or Firm* — Drinker Biddle & Reath LLP

(57) ABSTRACT

The present invention relates to a process for producing porous or finely divided solid inorganic materials, the surface of which has been modified with at least one organic substance, under supercritical conditions, wherein the supercritical conditions are lowered by addition of an inert organic substance.

15 Claims, No Drawings

PROCESS FOR PRODUCING POROUS OR FINELY DIVIDED SOLID INORGANIC MATERIALS

CROSS-REFERENCE TO RELATED APPLICATIONS

This application claims the benefit of U.S. Provisional Application 61/760,679, filed Feb. 5, 2013, which is incorporated herein by reference.

The present invention relates to a process for producing porous or finely divided solid inorganic materials, the surface of which has been modified with at least one organic substance.

Porous oxidic materials are of interest for numerous applications, for example as adsorbents, fillers, release agents, thickeners, dispersing aids, free-flow aids, defoamers, matting additives, active ingredient carriers and/or catalyst supports. Among the porous, solid oxidic materials, the class of aerogels is of particular significance. Aerogels are porous, solid oxidic materials generally consisting of silicon oxides, i.e. silica, or metal oxides. Aerogels, especially aerogels of silica, are of excellent suitability as thermal insulation material because their thermal conductivity is only low, or as support material for catalysts because their specific surface area is high. Further fields of use of aerogels are in the fields of plastics, for example natural and synthetic rubbers, adhesives, paints, coatings, pharmaceuticals, cosmetics, the paper, textile, mineral oil and fiber industry, and glass technology, pyrotechnology and foundry technology, where the aerogels find various uses as dispersing aids, reinforcers, free-flow aids, antisettling agents, fillers, defoamers, matting additives, active ingredient carriers and/or absorbents.

Finely divided, solid inorganic materials, particularly because of their morphology, i.e. their three-dimensional structure, are of interest for numerous applications, for example as catalyst support materials, in fuel cells, as gas storage materials, for active ingredient and effect substance release, in filter systems, in the textile industry and in the electronics industry. Finely divided, solid inorganic materials may, for example, be in the form of finely divided inorganic structures. These are generally structures having spatial dimensions on the nanometer or micrometer scale, for example finely divided hollow spheres, fibers, platelets or agglomerates of primary particles having dimensions in the nanometer range. For example, it is possible to encase molecules in hollow nanospheres or to use nanofibers as electrical conductors in molecular electronics. A further property of interest of finely divided inorganic structures is the high specific surface area thereof. This allows enhancement of interactions with the surrounding phase, such that catalysis and/or adsorption processes, for example, can run faster.

Porous or finely divided solid inorganic materials, the surfaces of which have been modified with at least one organic substance, can be produced by different processes. A common feature of these processes is that the modification with at least one reactive organic substance comprises a treatment of the porous or finely divided solid inorganic material with a reactive substance under supercritical conditions.

The production of porous, solid oxidic materials, for example aerogels, which can be surface-modified by the process according to the invention, is generally possible by dewatering hydrated forms of the oxidic materials, called hydrogels. However, this dewatering operation is associated with a number of problems. The removal of the water from the hydrogel by simply heating can lead to the collapse of the hydrogel or to the crystallization of the oxidic material, such that the resulting oxidic material is compact and has only low porosity, if any. In order to avoid these problems, the hydrogel can be generated and immediately dried in situ, for example by spraying waterglass and mineral acid in a spray drying apparatus.

It is known that the water present in the hydrogel can be displaced by treatment with a lower-boiling water-soluble liquid, for example volatile alkanols such as methanol, ethanol or isopropanol, and that the dewatered material obtained (this is generally referred to as an organogel, called an alcogel when alcohols are used) can be dried under supercritical conditions (see, for example, U.S. Pat. No. 2,249,767). EP 171722 discloses performing such a supercritical drying operation in $CO_2$.

For many applications, especially in the case of use as thermal insulation material, the absorption of water into the porous, solid oxidic material is undesirable, since the material ages in the process and its advantageous properties are lost. The drying of the dewatered material, i.e. the organogel, in the presence of alcohols leads to a certain hydrophobization, since the alcohol molecules, through their OH groups, can enter into a chemical bond with the surface of the oxidic material.

Known hydrophobizing reagents include further compounds, for example organosilicon compounds, with which the dewatered, i.e. dried, hydrogel, i.e. the organogel, is treated in the gas phase or which may also already be present in the course of precipitation, intermediate process steps or supercritical drying. The coverage of the surface with hydrophobic compounds is supposed to prevent the porous, solid oxidic material from absorbing water again.

For the reasons mentioned, there is thus a need for processes for surface modification of porous, solid inorganic materials, especially porous, solid oxidic materials.

The production of fine structures from inorganic materials which can be surface modified by the process according to the invention is known in principle, for example from WO 03/034979 and WO 2010/122049, or these are produced by standard processes, for example by sol-gel processes in polyphasic systems or by sol-gel processes in conjunction with electrospinning.

For a wide variety of different applications, it is advantageous to modify the surface of the finely divided inorganic structures with organic molecules. This allows control of the properties of the inorganic structures, for example electrical conductivity, hydrophilicity/lipophilicity, adsorption capacity or optical properties. For many applications, it is of interest to perform the modification of the inorganic structures subsequently, i.e. after the synthesis and optionally purification and/or isolation thereof.

A problem in the subsequent surface modification of the finely divided inorganic structures, however, is the mechanical instability thereof compared to "bulk" nanoparticles in the form of unstructured, mechanically robust powders. Especially the finely divided inorganic structures formed from hard inorganic materials are brittle and mechanically fragile. Conventional wet-chemical methods for surface modification frequently lead to the destruction of the finely divided inorganic structures due to the mechanical stress which occurs. This mechanical stress may be attributable to forces which occur, for example, in the course of mixing and stirring, and in vapor bubble formation and/or outgassing processes. Capillary forces can also lead to the destruction of the finely divided inorganic structures.

It has been found that a particularly low degree of destruction of the finely divided, inorganic structures is achieved when the surface modification of the structures is effected under supercritical conditions.

WO 95/06617 describes a process for producing hydrophobized silica aerogels having improved properties, which comprises the reaction of a waterglass solution with an acid, washing the hydrogel formed with water to remove ionic constituents, treatment of the hydrogel with an alcohol, especially isopropanol, and supercritical drying of the resulting alcogel in the presence of the alcohol. However, the hydrophobization achieved, more particularly the long-term stability thereof, is unsatisfactory.

The surface modified porous or finely divided solid inorganic materials produced according to the prior art have the disadvantages that the supercritical conditions required during the reaction require high temperatures and high pressures. High temperatures and high pressures make particular demands on the reaction vessels used and the further apparatus constructions used. High-pressure reaction vessels, for example autoclaves, are expensive. Conducting the reaction at high temperatures and high pressures additionally represents a higher endangerment potential in principle. Moreover, more energy has to be expended in order to obtain high temperatures and high pressures.

There is therefore a need for processes for surface modification of porous or finely divided solid inorganic materials which allow a high degree of modification of the surface with the reactive molecules, such that, for example, the resulting surface modified aerogels exhibit only low water absorption and thus have long-term stability, and surface modified finely divided inorganic structures are destroyed only to a minor degree, if at all, at high surface coverage. These processes are not to have the disadvantages described above.

It has now been found that, surprisingly, said disadvantages can be overcome by a process for producing porous or finely divided solid inorganic materials, the surface of which has been modified with at least one organic substance, in which the porous or finely divided solid inorganic materials are treated with an organic liquid comprising at least one reactive organic substance which can react with the surface of the inorganic material and which has at least one reactive functional group selected from hydroxyl groups, especially carbon-bonded hydroxyl groups, carboxyl groups, carbonate groups, and oxygen atoms bonded to phosphorus atoms, and which additionally comprises at least one inert organic substance. In this context, the inert organic substance is selected such that the mixture of reactive and inert organic substance has a critical point at a lower temperature and/or lower pressure than the critical point of the reactive organic substance.

By addition of an inert organic substance to the reactive organic substance, it is possible to lower the critical temperature and/or the critical pressure of the mixture. At the same time, surprisingly, not only are the advantageous properties of the porous or finely divided solid inorganic materials, such as low water absorption capacity, preserved. Instead, it is possible in this way to further reduce the degree of destruction of the finely divided solid inorganic materials.

The invention therefore relates to a process for producing porous or finely divided solid inorganic materials, the surface of which has been modified with at least one organic substance, comprising a treatment with an organic liquid under supercritical conditions, the organic liquid being a mixture of at least one reactive organic substance which can react with the atoms of the inorganic material to form a chemical bond and which has at least one reactive functional group selected from hydroxyl groups, especially carbon-bonded hydroxyl groups, carboxyl groups, carbonate groups, and oxygen atoms bonded to phosphorus atoms, and at least one inert organic substance, wherein the mixture has a critical point which is at lower temperature and/or lower pressure than the critical point of the reactive organic substance.

The porous, solid inorganic materials produced in the process according to the invention are especially produced by the following steps:

a) providing a hydrogel of the inorganic material,
b) removing the water by treating the hydrogel with an anhydrous organic liquid and
c) drying the treated hydrogel, i.e. the organogel obtained in step b), under supercritical conditions in the presence of the organic liquid.

The porous, solid inorganic materials produced in the process according to the invention have the advantages of only low water absorption and high long-term stability. It has also been found that, when relatively low temperatures and/or relatively low pressures are used in the process according to the invention, the proportion of destroyed porous, solid inorganic materials, usually obtained in the form of fine powder, can be reduced, especially in the production of porous, solid inorganic materials of low density. The reactive organic substances used in the process according to the invention may particularly be inexpensive compounds, for example polyhydric alcohols, hydroxycarboxylic acids, phosphates, polyphosphates and/or polycarboxylic acids.

The starting materials used for production of the porous, solid inorganic materials are preferably inorganic hydrogels, i.e. hydrogels based on semimetal or metal oxides, particularly hydrogels based on silicon dioxide, zinc oxide, tin(IV) oxide, titanium(IV) oxide, cerium(IV) oxide and aluminum oxide, especially based on silicon dioxide. The proportion of hydrogels which are based on semimetal or metal oxides and are used with preference is generally at least 90% by weight, especially at least 95% by weight, based on the total amount of the hydrogels used.

Processes for producing hydrogels which give rise to the porous, solid inorganic materials are known in principle, for example from the prior art cited at the outset. In general, the hydrogels are produced by hydrolysis of suitable metal oxide precursors, for example metal salts or covalent metal compounds or semimetal compounds such as (semi)metal halides or (semi)metal alkoxides, optionally followed by a partial condensation of the (semi)metal hydroxides or (semi)metal oxide hydroxides formed in the hydrolysis.

For example, hydrogels based on silicon dioxide are generally produced by condensation of alkali metal waterglass, especially sodium waterglass. This is typically done by mixing a waterglass solution, for example a 10 to 30 percent by weight, preferably 12 to 20 percent by weight, waterglass solution, with a dilute aqueous acid, for example a 1 to 50 percent by weight, especially 5 to 40 percent by weight, acid, especially an aqueous mineral acid, preferably sulfuric acid. Preference is given to using a sufficient amount of acid that a pH of 7.5 to 11, especially 8 to 11, more preferably 8.5 to 10, most preferably 8.5 to 9.5, is established in the mixed product. Especially suitable for this process is the use of a mixing nozzle from which the mixture of waterglass solution and dilute mineral acid is sprayed, and where the sol formed in the course of mixing solidifies in the air during the aerial phase to form hydrogel droplets. It is of course also possible, for example, to produce hydrogel moldings by combining waterglass and dilute acid in suitable form and then to allow gelation.

Prior to removal of the water, preference is given to freeing the hydrogel of ionic constituents by washing with water or dilute aqueous solutions of inorganic bases, preference being given to proceeding in such a way that the pH of the hydrogel barely changes, i.e. less than 2 pH units, especially less than 1 pH unit, and corresponds virtually to the value established in the mixed product. The inorganic bases used may, for example, be aqueous solutions of alkali metal hydroxides such as sodium hydroxide solution or aqueous ammonia. The procedure here will preferably be such that the hydrogel, even after the washing operation, has a pH within the range mentioned of 7.5 to 11, preferably 8.5 to 10, more preferably 9 to 10. The washing operation is preferably conducted until the conductivity of the washing water flowing away is about 20 to 300 µS/cm, preferably 50 to 150 µS/cm. This corresponds to an alkali metal (sodium) content of the hydrogel of generally 0.1 to 1.7% by weight, preferably 0.4 to 1.3% by weight, determined on a sample dried at 10 mbar and 80° C. for 12 h.

The hydrogels produced in accordance with the invention may also, as described in DE 3914850, contain pigments, in which case suitable pigments are especially those which scatter, absorb or reflect infrared radiation of wavelength 3 to 10 µm. Such pigments are generally added to the hydrogel at an early stage, in the course of production thereof.

Preference is given to removing the water from the hydrogel by treatment with a water-miscible organic liquid. The water-miscible organic liquid used for removal of the water is essentially anhydrous, i.e. it generally has a water content of not more than 5% by weight, particularly 0 to 2% by weight and especially 0 to 1% by weight, based on the overall water-miscible liquid.

The treatment of the hydrogel with the water-miscible anhydrous organic liquid substantially or especially virtually completely replaces the aqueous phase present in the hydrogel with the substantially or essentially anhydrous water-miscible organic liquid. For treatment of the hydrogel with the water-miscible anhydrous organic liquid, the hydrogel is contacted with the liquid, and then the treated product is separated from the liquid. For example, the hydrogel can be suspended in the water-miscible organic liquid and then the solid or gel constituents can be separated from the liquid phase, for example by filtration or centrifugation. Advantageously, the treatment is undertaken with the aid of a flow apparatus. For this purpose, the hydrogel is introduced into a suitable vessel having an inlet for the water-miscible organic liquid and an outlet, the inlet and outlet being arranged such that the water-miscible organic liquid flows through the hydrogel. The water-miscible organic liquid is fed in through the inlet, and the mixture of the water-miscible organic liquid and water is drawn off via the outlet. The treatment is preferably conducted until the water content of the organic phase flowing away is less than 2% by volume, preferably less than 1% by volume.

The temperature at which the treatment is undertaken is typically in the range from 0 to 60° C., preferably in the range from 10 to 50° C., for example 20 to 30° C. The treatment of the hydrogel with the anhydrous water-miscible organic liquid can, however, also be conducted at elevated temperature.

The removal of the water by treatment with the water-miscible organic liquid is preferably effected under subcritical conditions. Preference is given to removing the water under ambient pressure. Another possibility is exchange under reduced pressure or under elevated pressure. Typically, the treatment of the hydrogel with the water-miscible liquid is effected at ambient pressure.

As a result of the water exchange in the hydrogel, what is called an organogel is obtained, in which the physically bound water has substantially been exchanged for the constituents of the water-miscible organic liquid.

The organic liquid used for treatment of the hydrogel is water-miscible, i.e. the liquid at 20° C. has no miscibility gap with water. Preference is given to liquids which have a boiling point at standard pressure in the range from 10 to 100° C., especially in the range from 10 to 90° C. The water-miscible liquid is preferably an organic solvent S or a mixture of organic solvents S consisting to an extent of at least 70% by weight, based on the total amount of the water-miscible organic liquid, of one or more organic solvents S which at 20° C. have no miscibility gap with water.

Preference is given to organic solvents S which have a boiling point at standard pressure in the range from 30 to 120° C., especially in the range from 30 to 100° C. The organic solvent S is preferably selected from $C_1$-$C_4$-alkanols, for example methanol, ethanol, n-propanol, isopropanol, n-butanol, isobutanol, 2-butanol and tert-butanol, $C_1$-$C_4$-alkanals such as formaldehyde, acetaldehyde, propionaldehyde, butyraldehyde and isobutyraldehyde, and $C_3$-$C_4$-ketones such as acetone or methyl ethyl ketone, and mixtures thereof. The organic solvent S is more preferably a $C_1$-$C_4$-alkanol. It is most preferably isopropanol.

The water-miscible organic liquid which is used in the removal of the water from the hydrogel may already comprise the reactive organic substance as defined below. Preferably, the organic liquid used in the removal of the water from the hydrogel already comprises the reactive organic substance. More preferably, the organic liquid used in the removal of the water comprises the reactive organic substance and the inert organic substance.

After the removal of the water from the hydrogel, the treated hydrogel thus obtained, i.e. the organogel, is treated by the process according to the invention.

In the process according to the invention, it is also possible to use finely divided solid inorganic materials. In that case, the process according to the invention preferably comprises the following steps:

a') providing a finely divided solid inorganic material having an unmodified surface and b') treating the material provided in step a') with the organic liquid under supercritical conditions.

The finely divided solid inorganic materials usable in the process according to the invention are, in particular, finely divided hard inorganic structures.

Finely divided, solid, in particular hard, inorganic structures are understood to mean structures having, in at least one spatial direction, a material thickness M of not more than 1000 nm and, as an overall structure, having a dimension of at least 5 times the material thickness M in at least one spatial direction. The material thickness M may, for example, be the wall thickness of the sphere shell of a hollow sphere, the diameter of a fiber, the thickness of a platelet, or the diameter of individual primary particles which form an agglomerate. The dimension of the overall structure may, for example, be the diameter of a hollow sphere, the length of a fiber, the greatest dimension of a platelet or the greatest dimension of the agglomerate.

The finely divided solid, in particular hard, inorganic structures generally have, in at least one spatial direction, a material thickness M of not more than 1000 nm, especially in the range from 2 to 500 nm, and as an overall structure have, in at least one spatial direction, a dimension which is at least 5 times, especially at least 10 times, the material thickness M.

The finely divided, solid, in particular hard, inorganic structures preferably have, as an overall structure, in at least one spatial direction, a dimension in the range from 10 µm to 10 cm, more preferably in the range from 10 µm to 5 cm, most preferably in the range from 10 µm to 1 cm.

Suitable finely divided solid, in particular hard, inorganic structures for the process according to the invention are especially the following:

i. hollow spheres whose sphere shell has a thickness of not more than 100 nm and especially in the range from 2 to 50 nm, and where the ratio of sphere diameter to thickness of the sphere shell is at least 5, particularly at least 7, especially at least 10 and is, for example, in the range from 5 to 200, particularly in the range from 7 to 150 and especially in the range from 10 to 100;

ii. fibers having a fiber thickness of not more than 1000 nm, particularly 50 to 500 nm, and an aspect ratio of at least 50, particularly at least 100, for example in the range from 50 to 5000, particularly in the range from 100 to 2000;

iii. platelets having a thickness of not more than 100 nm and a ratio of diameter to thickness of at least 5, particularly at least 10, for example in the range from 5 to 200, particularly in the range from 7 to 150 and especially from 10 to 100;

iv. agglomerates of particles having a mean particle diameter of not more than 100 nm, especially 2 to 80 nm, the proportion by volume of the inorganic material, based on the total volume of the agglomerate, being in the range from 1 to 20% by volume.

The finely divided solid, in particular hard, inorganic materials, preferably finely divided hard inorganic structures, used in the process according to the invention may be unfunctionalized, i.e. may not yet have been treated with a reactive substance, or may already be partly functionalized. Preference is given to using finely divided solid inorganic materials, preferably finely divided hard inorganic structures, which are unfunctionalized, i.e. have less than 3% by weight, preferably less than 1% by weight or less than 0.1% by weight of reactive organic substance, based on the total weight of the finely divided solid inorganic materials, on the surface.

The material of which the finely divided hard inorganic structures are composed generally has a Mohs hardness of greater than 4, especially a Mohs hardness in the range from 4.5 to 9, preferably in the range from 5 to 7.

The solid, in particular hard, inorganic material is preferably selected from metal oxides and semimetal oxides.

More particularly, the solid, in particular hard, inorganic material comprises, as a main component, i.e. in an amount of 90 to 100% by weight, based on the total weight of the solid, in particular hard, inorganic material, at least one of the oxides from the group of silicon dioxide, zinc oxide, tin(IV) oxide, titanium(IV) oxide and aluminum oxide. More particularly, the solid, in particular hard, inorganic material comprises, as a main component, i.e. in an amount of 90 to 100% by weight, based on the total weight of the solid, in particular hard, inorganic material, at least one of the oxides from the group of silicon dioxide, titanium(IV) oxide and aluminum oxide or a mixture of these oxides with at least one further oxide from the group of zinc oxide and tin(IV) oxide. Specifically, the solid, in particular hard, inorganic material comprises, as a main component, i.e. in an amount of 90 to 100% by weight, based on the total weight of the solid, in particular hard, inorganic material, silicon dioxide.

Fine structures composed of inorganic hard materials are known in principle, for example from WO 03/034979 and WO 2010/122049, or can be produced by standard processes, for example by sol-gel processes in polyphasic systems or by sol-gel processes in conjunction with electrospinning.

According to the invention, the porous or finely divided solid inorganic materials are subjected to a supercritical treatment with an organic liquid.

The concentration of the reactive organic substance in the organic liquid is generally selected such that the resulting mixture can be converted readily to the supercritical state.

In general, the concentration of the reactive organic substance in the organic liquid is therefore in the range from 0.01 to 50% by weight, especially in the range from 0.1 to 20% by weight, based on the total weight of the organic liquid. Accordingly, the reactive organic substance is generally used in an amount in the range from 0.01 to 50% by weight, especially in the range from 0.1 to 20% by weight, based on the total weight of the organic liquid.

The reactive organic substance has at least one reactive functionality F, for example 1 to 10 or 1 to 5 reactive functionalities F. The reactive compound preferably has one, two or three reactive functionalities F. Reactive functionalities F are understood in the context of the invention to mean atoms and/or atom groups which can react with the atoms of the porous or finely divided solid inorganic material to form a chemical bond, preferably a covalent chemical bond, and which are selected from hydroxyl groups, especially carbon-bonded hydroxyl groups, carboxyl groups, carbonate groups, and oxygen atoms bonded to phosphorus atoms.

According to the invention, the reactive functionalities F are selected from hydroxyl groups, especially carbon-bonded hydroxyl groups, carboxyl groups, carbonate groups, and oxygen atoms bonded to phosphorus atoms. More particularly, the reactive functionalities F are selected from hydroxyl groups, preferably carbon-bonded hydroxyl groups, carboxyl groups and carbonate groups.

If the reactive organic substance has one reactive functionality F, the reactive organic substance is preferably selected from $C_1$-$C_6$-alkanols, for example methanol, ethanol, n-propanol, isopropanol, n-butanol, isobutanol, 2-butanol and tert-butanol;

$C_1$-$C_6$-alkanecarboxylic acids, for example formic acid, acetic acid, propionic acid, butyric acid and valeric acid; and mixtures thereof.

If the reactive organic substance has two or more reactive functionalities F, the reactive organic substance is preferably selected from $C_2$-$C_6$-alkanepolycarboxylic acids, i.e. polybasic, e.g. di- or tribasic, linear or branched alkanecarboxylic acids having two to six carbon atoms. Examples are oxalic acid, malonic acid, succinic acid, glutaric acid, adipic acid and maleic acid;

hydroxy-$C_2$-$C_6$-alkanemono- and -polycarboxylic acids, i.e. mono- or polybasic, e.g. mono-, di- or tribasic, linear or branched alkanecarboxylic acids having two to six carbon atoms, which have at least one hydroxyl group in addition to at least one carboxyl group. Examples are lactic acid, 2-hydroxybutanoic acid and citric acid;

$C_2$-$C_6$-alkanepolyols, e.g. di- or trihydric, linear or branched aliphatic alcohols having two to six carbon atoms. Examples are ethylene glycol, 1,2-propanediol, 1,3-propanediol, neopentyl glycol and glycerol;

$C_3$-$C_6$-cycloalkanepolyols, i.e. polyhydric, e.g. di- or trihydric, cycloaliphatic alcohols having three to six carbon atoms, such as 1,2-cyclopropanediol, 1,2-cyclopentanediol and 1,2-cyclohexanediol;

2-hydroxyphenol (catechol) and mono- and di-$C_1$-$C_4$-alkyl-2-hydroxyphenols, especially mono- and dimethyl-2-hydroxyphenols;

$C_2$-$C_4$-alkylene carbonates, i.e. cyclic esters of carbonic acid with $C_2$-$C_4$-alkanediols, e.g. ethylene carbonate (1,3-dioxolan-2-one) and propylene carbonate (4-methyl-1,3-dioxolan-2-one);

phosphates, polyphosphates, $C_1$-$C_8$-alkyl mono- and polyphosphates;

and mixtures thereof.

The reactive organic substance is preferably selected from $C_1$-$C_6$-alkanols, $C_1$-$C_6$-alkanecarboxylic acids, $C_2$-$C_6$-alkanepolycarboxylic acids, $C_2$-$C_6$-alkanepolyols, $C_2$-$C_4$-alkylene carbonates and mixtures thereof.

The reactive organic substance is further preferably selected from $C_1$-$C_4$-alkanols, mixtures of at least two $C_1$-$C_4$-alkanols and mixtures of at least one $C_1$-$C_4$-alkanol with at least one further reactive organic substance selected from $C_2$-$C_6$-alkanepolyols, $C_2$-$C_4$-alkylene carbonates and $C_2$-$C_6$-alkanepolycarboxylic acids.

Particularly preferred reactive organic substances are 2-hydroxyphenol, $C_1$-$C_4$-alkyl-2-hydroxyphenols, $C_2$-$C_6$-alkanepolyols, especially ethylene glycol, 1,2-propanediol, 1,3-propanediol and glycerol, hydroxy-$C_2$-$C_6$-alkanemono- and -polycarboxylic acids, especially lactic acid and citric acid, $C_2$-$C_4$-alkylene carbonates, especially ethylene carbonate and propylene carbonate, and $C_2$-$C_6$-alkanepolycarboxylic acids, especially malonic acid and oxalic acid.

Very particularly preferred reactive organic substances are methanol, ethanol, isopropanol, tert-butanol, glycerol, ethylene glycol, 1,2-propanediol, 1,3-propanediol, 2-hydroxyphenol, oxalic acid, malonic acid, ethylene carbonate, propylene carbonate and mixtures thereof.

Especial reactive organic substances are methanol, ethanol, isopropanol, 1,2-propanediol, 1,3-propanediol, 2-hydroxyphenol, oxalic acid, malonic acid, ethylene carbonate, propylene carbonate and mixtures thereof.

The reactive organic substance is very especially isopropanol.

Suitable inert organic substances are organic substances which do not have any reactive functionality F and have a lower critical temperature and/or a lower critical pressure than the reactive organic substance.

The inert organic substance preferably has a critical temperature in the range from 20 to 300° C., especially in the range from 100 to 250° C.

The inert organic substance preferably has a critical pressure in the range from 20 to 80 bar, especially in the range from 20 to 50 bar.

The inert organic substance is especially selected from $C_1$-$C_8$-alkanes, $C_2$-$C_8$-alkenes, dialkyl ethers having a total carbon number in the range from 2 to 6, $C_3$-$C_4$ ketones, dichloromethane and mixtures thereof.

Suitable inert organic substances are particularly $C_2$-$C_8$-alkanes such as ethane, propane, n-butane, isobutane, n-pentane, isopentane, n-hexane and isomers thereof, and n-heptane and isomers thereof. Suitable inert organic substances are also $C_2$-$C_8$-alkenes such as ethene, propene, n-butene, 2-butene, isobutene, 1-pentene and 1-hexene. Also suitable are dialkyl ethers having a total carbon number in the range from 2 to 6, such as dimethyl ether, diethyl ether, methyl isopropyl ether, methyl tert-butyl ether, and $C_3$-$C_4$ ketones, namely acetone and methyl ethyl ketone, and also dichloromethane, and mixtures thereof.

In a preferred embodiment of the invention, the inert organic substance is a $C_3$-$C_8$-alkane, especially n-pentane, n-hexane or n-heptane, and the reactive organic substance is a $C_2$-$C_4$-alkanol, especially isopropanol.

The organic liquid preferably has a critical temperature $T_c$ in the range from 110 to 300° C.

The concentration of the inert organic substance in the organic liquid is generally in the range from 30 to 95% by weight, especially in the range from 40 to 80% by weight, based on the organic liquid.

The supercritical surface modification both of porous solid inorganic materials and of finely divided solid inorganic materials can be undertaken in a customary manner, for example in analogy to the prior art cited at the outset.

In general, a mixture of the organic liquid comprising the reactive organic substance is heated with, for example, the finely divided inorganic structures or, for example, the organogel, for example a suspension, under pressure to a temperature above the critical temperature.

The treatment under supercritical conditions is preferably effected at a temperature of not more than 40 K, especially not more than 20 K, above the critical temperature of the organic liquid.

In general, the temperature during the treatment is in the range from 100 to 300° C., preferably 150 to 250° C. The pressure required for this is typically in the range from 20 to 100 bar, preferably 20 to 60 bar.

In general, the procedure will be to introduce the materials to be treated under subcritical conditions into the organic liquid initially charged in a pressure vessel, for example an autoclave, and then to bring the liquid under supercritical conditions by heating under pressure, in such a way that the boiling temperature is not exceeded at the pressure existing in the reaction vessel at any time during the treatment. The mixture is preferably kept under supercritical conditions for 1 min to 8 h, especially 1 min to 4 h.

If porous solid inorganic materials, e.g. aerogels, are surface modified by the process according to the invention, the procedure will preferably be such that the treatment under supercritical conditions ("drying") directly follows the removal of the water.

After the desired reaction time, the organic liquid is removed from the pressure vessel by decompression, preferably isothermal decompression, preferably gradually by gently opening the pressure valve. Preference is given to conducting the decompression at a decompression rate in the range from 0.1 to 5 bar/min. During the supercritical surface reaction, the formation of any great volumes of gas through uncontrolled vaporization or outgassing will preferably be prevented by means of decompression, i.e. said removal of the gas mixture via the pressure valve.

The process according to the invention may be followed by further process steps. It is possible, for example, for further purification and workup steps to follow. These may, for example, be the purging of the pressure vessel with compressed air or gaseous nitrogen, in order particularly to remove residues of the organic liquid still present. The process according to the invention may also be followed by a subcritical, conventional drying operation at slightly elevated temperature, optionally while purging with compressed air or gaseous nitrogen. The process according to the invention may additionally be followed, for example, by steps for purification, for heat treatment and/or calcination, sieving and/or classification, compressing, bonding or immersion into active substances.

The process product of the process according to the invention is porous or finely divided solid inorganic materials.

The surface of these inorganic materials has been modified with the reactive organic substance. The degree of surface coverage can be determined, for example, via the carbon content determined in the elemental analysis.

The carbon content of the surface modified porous solid inorganic materials is preferably in the range from 0.1 to 15% by weight, especially in the range from 1.5 to 13% by weight, based on the total weight of the surface functionalized porous solid inorganic materials.

The carbon content of the surface modified finely divided solid inorganic materials is preferably in the range from 0.1 to 15% by weight, especially in the range from 1.5 to 13% by weight, based on the total weight of the surface functionalized finely divided solid inorganic materials.

The finely divided solid inorganic material obtainable by the process according to the invention comprises an inorganic material selected from metal oxides and semimetal oxides and, as a main constituent, especially at least one oxide in an amount of 90 to 100% by weight, based on the total weight of the inorganic material selected from silicon dioxide, zinc oxide, tin(IV) oxide, titanium(IV) oxide and aluminum oxide.

The porous solid inorganic material obtainable by the process according to the invention, owing to the treatment with the reactive organic substance, has improved properties, especially a hydrophobized surface and lower water absorption, even in the case of prolonged water contact.

Owing to the high porosity, the porous solid inorganic material only has low bulk densities of about 25 to 300 g/L, preferably 50 to 200 g/L, more preferably 100 to 150 g/L. The proportion of pores in the total volume of the material is about 50 to 98% by volume, especially 75 to 97% by volume.

In preferred embodiments of the invention, the porous solid inorganic material obtainable in accordance with the invention comprises, as a main component, i.e. in an amount of 90 to 100% by weight, based on the total weight of the porous solid inorganic material, at least one oxide from the group of silicon dioxide, zinc oxide, tin(IV) oxide, titanium(IV) oxide, cerium(IV) oxide and aluminum oxide. More particularly, the porous solid inorganic material obtainable in accordance with the invention comprises, as a main component, i.e. in an amount of 90 to 100% by weight, based on the total weight of the porous solid inorganic material, at least one oxide from the group of silicon dioxide, titanium(IV) oxide and aluminum oxide or a mixture of these oxides with at least one further oxide from the group of zinc oxide, tin(IV) oxide and cerium(IV) oxide. Specifically, the porous solid inorganic material comprises, as a main component, i.e. in an amount of 90 to 100% by weight, based on the total weight of the porous solid inorganic material, at least one oxide from the group of silicon dioxide.

The porous solid inorganic material is preferably an aerogel. The porous solid inorganic material is more preferably an aerogel based on silicon dioxide.

The porous solid inorganic material obtained by the process according to the invention can be used either in the form of granules (typical particle sizes from 1 to 8 mm) or after prior grinding or the like as powder (particle sizes of less than 1 mm) for different purposes, for example as described in the introduction.

The porous solid inorganic material obtainable by the process according to the invention generally has a density in the range from 0.025 to 0.30 g/cm$^3$.

The materials obtainable by the process according to the invention are suitable for a multitude of applications.

The examples which follow serve to illustrate the invention and should not be understood in a limiting manner.

EXAMPLES

Chemicals Used:
waterglass solution (techn., from Woellner)
sodium oxide (80%, from Sigma-Aldrich)
sulfuric acid (>95%, from Sigma-Aldrich)
isopropanol (>99.9%, from BCD Chemie)
n-pentane (98%, from Sigma-Aldrich)
n-hexane (98%, from Sigma-Aldrich)
n-heptane (98%, from Sigma-Aldrich)
ethanol (99.8%, from Sigma-Aldrich)
ethylene glycol (99.8%, from Sigma-Aldrich)
Analysis:
Bulk density based on ISO 3944
Specific surface area by adsorption of nitrogen according to BET at a temperature of −196° C. to DIN ISO 9277
Elemental analysis (carbon content): vario MICRO cube (from Elementar, CHN operating mode at 1000° C.)
Contact angle measurements to DIN 55660

Preparation Example 1

Preparation of a Hydrogel Based on Silica

A 13% by weight waterglass solution was prepared by diluting a technical waterglass solution comprising 27% by weight of silicon dioxide and 8% by weight of sodium oxide with water.

In a mixing nozzle, at 20° C. and 2.5 bar, 45.7 L/h of the 13% by weight waterglass solution prepared were combined with 6 L/h of a 23% by weight aqueous sulfuric acid solution. The unstable hydrosol which formed as a result of progressive neutralization of the waterglass solution in the mixing chamber had a pH of 8.1±0.1 and, after a residence time of 0.1 s, was sprayed through the nozzle mouth (diameter 2 mm). As it flew through the air, the liquid jet separated into individual droplets, which solidified to give transparent, mechanically stable hydrogel spheres before hitting the water basin. The hydrogel obtained in this way was washed with demineralized water until the wash liquid flowing away had an electrical conductivity of less than 110 μS/cm and a pH of 9.8±0.1. The sodium content of a sample of the hydrogel dried at 80° C. in a water jet vacuum was 1.1% by weight.

Preparation Example 2

Preparation of a Hydrogel Based on Silica with Reduced Silicon Dioxide Density

A hydrogel was prepared analogously to preparation example 1, except that an 11% waterglass solution was provided by dilution and combined with a 20.5% aqueous sulfuric acid solution in a mixing nozzle. Analogously to preparation example 1, hydrogel spheres which had a reduced silicon dioxide density were obtained.

Preparation Example 3

Preparation of an Alcogel Based on Isopropanol 2000 g of the hydrogel from preparation example 1 were introduced into a 5 L vessel, which was filled completely with isopropanol. At 25° C., anhydrous isopropanol was pumped through the vessel until the water content of the isopropanol flowing away was less than 0.1% by volume. This required about 8 L of isopropanol.

Preparation Example 4

Preparation of an Alcogel Based on Ethanol 2000 g of the hydrogel from preparation example 1 were introduced into a 5 L vessel, which was filled completely with ethanol. At 25° C., anhydrous ethanol was pumped through the vessel until the water content of the ethanol flowing away was less than 0.1% by volume. This required about 8 L of ethanol.

Preparation Example 5

Preparation of an Alcogel Based on Isopropanol with Reduced Silicon Dioxide Density 2000 g of the hydrogel from preparation example 2 were introduced into a 5 L vessel, which was filled completely with isopropanol. At 25° C., anhydrous isopropanol was pumped through the vessel until the water content of the isopropanol flowing away was less than 0.1% by volume. This required about 8 L of isopropanol.

Preparation Example 6

Silicon Dioxide Nanoparticle Agglomerates

In a mixing chamber, 2 L of 13% by weight industrial waterglass solution and 1 L of 23% by weight sulfuric acid were combined. The sol formed through neutralization of the waterglass solution was sprayed through a nozzle of diameter 2 mm. During the flight through the air, the liquid jet broke down to individual droplets, which gelated before arriving in a water basin and solidified to give transparent, mechanically stable spheres which agglomerated to nanoparticle agglomerates. The nanoparticle agglomerates were washed with demineralized water until the wash liquid flowing away had an electrical conductivity of about 150 µS/cm. Then the water present in the nanoparticles was exchanged for isopropanol. To this end, 1 kg of the silicon dioxide nanoparticle agglomerates was introduced into a vessel of capacity 5 L, which was filled completely with isopropanol. At 25° C., isopropanol was pumped through the vessel until the water content of the isopropanol flowing away was less than 0.1% by volume. This required about 5 L of isopropanol. The silicon dioxide nanoparticle agglomerates were separated from the liquid phase by filtration.

This gave silicon dioxide nanoparticle agglomerates having an average agglomerate diameter of about 1 to 8 mm and an average diameter of the primary nanoparticles of about 1 to 20 nm, determined by means of light microscopy and scanning electron microscopy. The bulk density of the silicon dioxide nanoparticle agglomerates was 750 g/L at solids content 13% (water content 87% by weight), corresponding, with unchanged volume, to a bulk density of the pure solid of about 100 g/L. The carbon content of the silicon dioxide nanoparticle agglomerates was less than 0.1% by weight.

Comparative Example 1

Isopropanol

2 L of the alcogel from preparation example 3 together with 6 L of isopropanol were introduced into a heatable stainless steel (RA4) pressure vessel having an internal sieve basket and a capacity of 20 L and the mixture was heated to 270° C. within 5 h, in the course of which the pressure in the pressure vessel was limited to 70 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 115 g/L. The specific surface area was 330 m$^2$/g. The carbon content was 6% by weight.

Variation a): The mixture was heated to 240° C. within 5 h, in the course of which the pressure in the pressure vessel was limited to 50 bar. The bulk density of the material obtained was 120 g/L. The specific surface area was 340 m$^2$/g. The carbon content was 6% by weight.

Variation b): The mixture was heated to 220° C. within 5 h, in the course of which the pressure in the pressure vessel was limited to 35 bar (subcritical conditions). The bulk density of the material obtained was 160 g/L. The specific surface area was 300 m$^2$/g. The carbon content was 5% by weight. When the pressure and/or the temperature was lowered further, the bulk density of the material obtained increased further.

Comparative Example 2

Isopropanol

2 L of the alcogel from preparation example 5 together with 6 L of isopropanol were introduced into a heatable stainless steel (RA4) pressure vessel having an internal sieve basket and a capacity of 20 L and the mixture was heated to 270° C. within 5 h, in the course of which the pressure in the pressure vessel was limited to 70 bar. This was followed by isothermal decompression within 60 min. The cooled reaction product was withdrawn and subjected to further drying at 80° C. and 200 mbar for about 2 h.

About 80% by weight of the aerogel obtained was in the form of granules having a particle size distribution of about 1 to 8 mm. The bulk density was 100 g/L. About 20% by weight of the product was in the form of fines (powder) with elevated bulk density. The specific surface area was 350 m$^2$/g. The carbon content was 6% by weight.

Comparative Example 3

Ethanol

2 L of the alcogel from preparation example 4 together with 6 L of ethanol were introduced into a heatable stainless steel (RA4) pressure vessel having an internal sieve basket and a capacity of 20 L and the mixture was heated to 270° C. within 5 h, in the course of which the pressure in the pressure vessel was limited to 80 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 125 g/L. The specific surface area was 340 m$^2$/g. The carbon content was 5% by weight.

Comparative Example 4

Isopropanol 500 g of the isopropanol-comprising silicon dioxide nanoparticle agglomerates from preparation example 6 were introduced together with 2 L of isopropanol into a heatable stainless steel (RA4) pressure vessel having an internal sieve basket and a capacity of 20 L. The reaction mixture was heated to 270° C. within 5 h, in the course of which the pressure was limited to 70 bar. Thereafter, the reaction mixture was decompressed isothermally within 90 min. The cooled product was withdrawn and dried at 70° C. and 0.2 bar for about 2 h.

Surface-modified silicon dioxide nanoparticle agglomerates were obtained with about the same dimensions as the unmodified silicon dioxide nanoparticle agglomerates. The bulk density of the agglomerates obtained was about 110 g/L. The specific surface area of the agglomerates was about 300 to 400 m$^2$/g. The carbon content of the agglomerates was about 6% by weight.

Example 1

Isopropanol, N-pentane; Volume Ratio 1:1

2 L of the alcogel from preparation example 3 together with a mixture of 3 L of isopropanol and 3 L of n-pentane were introduced into a heatable stainless steel (RA4) pressure vessel having an internal sieve basket and a capacity of 20 L and the mixture was heated to 220° C. within 4 h, in the course of which the pressure in the pressure vessel was limited to 35 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 110 g/L. The specific surface area was 320 m$^2$/g. The carbon content was 6% by weight.

Example 2

Isopropanol, N-hexane; Volume Ratio 1:1

2 L of the alcogel from preparation example 3 together with a mixture of 3 L of isopropanol and 3 L of n-hexane were introduced into a heatable stainless steel (RA4) pressure vessel having an internal sieve basket and a capacity of 20 L and the mixture was heated to 250° C. within 4 h, in the course of which the pressure in the pressure vessel was limited to 30 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 120 g/L. The specific surface area was 340 m$^2$/g. The carbon content was 6% by weight.

Example 3

Isopropanol, N-heptane; Volume Ratio 1:1

2 L of the alcogel from preparation example 3 together with a mixture of 3 L of isopropanol and 3 L of n-heptane were introduced into a heatable stainless steel (RA4) pressure vessel having an internal sieve basket and a capacity of 20 L and the mixture was heated to 270° C. within 4 h, in the course of which the pressure in the pressure vessel was limited to 28 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 110 g/L. The specific surface area was 320 m$^2$/g. The carbon content was 6% by weight.

Example 4

Ethanol, N-pentane; Volume Ratio 1:1

2 L of the alcogel from preparation example 3 together with a mixture of 3 L of ethanol and 3 L of n-pentane were introduced into a heatable stainless steel (RA4) pressure vessel having an internal sieve basket and a capacity of 20 L and the mixture was heated to 220° C. within 4 h, in the course of which the pressure in the pressure vessel was limited to 40 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 130 g/L. The specific surface area was 330 m$^2$/g. The carbon content was 5% by weight.

Example 5

Isopropanol, Ethylene Glycol, N-pentane; Volume Ratio 1:0.02:1

2 L of the alcogel from preparation example 3 together with a mixture of 3 L of isopropanol, 3 L of n-pentane and 60 mL of ethylene glycol were introduced into a heatable stainless steel (RA4) pressure vessel having an internal sieve basket and a capacity of 20 L and the mixture was heated to 220° C. within 4 h, in the course of which the pressure in the pressure vessel was limited to 35 bar. This was followed by isothermal decompression within 60 min. The cooled reaction product was withdrawn and subjected to further drying at 80° C. and 200 mbar for about 2 h.

The resulting aerogel was in the form of granules having a particle size distribution of about 1 to 8 mm. The bulk density was 110 g/L. The specific surface area was 315 m$^2$/g. The carbon content was 6% by weight.

Example 6

Isopropanol, N-pentane; Volume Ratio 1:1

2 L of the alcogel from preparation example 5 together with a mixture of 3 L of isopropanol and 3 L of n-pentane were introduced into a heatable stainless steel (RA4) pressure vessel having an internal sieve basket and a capacity of 20 L and the mixture was heated to 220° C. within 4 h, in the course of which the pressure in the pressure vessel was limited to 35 bar. This was followed by isothermal decompression within 60 min. The cooled reaction product was withdrawn and subjected to further drying at 80° C. and 200 mbar for about 2 h.

About 90% by weight of the resulting aerogel was in the form of granules having a particle size distribution of about 1 to 8 mm. The bulk density was 90 g/L. About 10% by weight of the product was in the form of fines (powder) having slightly elevated bulk density. The specific surface area was 390 m$^2$/g. The carbon content was 7% by weight.

Example 7

Isopropanol, N-hexane; Volume Ratio 1:1

2 L of the alcogel from preparation example 5 together with a mixture of 3 L of isopropanol and 3 L of n-hexane were introduced into a heatable stainless steel (RA4) pressure vessel having an internal sieve basket and a capacity of 20 L and the mixture was heated to 250° C. within 4 h, in the course of which the pressure in the pressure vessel was limited to 30 bar. This was followed by isothermal decompression within 60 min. The cooled reaction product was withdrawn and subjected to further drying at 80° C. and 200 mbar for about 2 h.

About 90% by weight of the resulting aerogel was in the form of granules having a particle size distribution of about 1 to 8 mm. The bulk density was 85 to 90 g/L. About 10% by weight of the product was in the form of fines (powder) having slightly elevated bulk density. The specific surface area was 380 $m^2/g$. The carbon content was 6% by weight.

Example 8

Isopropanol, N-heptane; Volume Ratio 1:1

2 L of the alcogel from preparation example 5 together with a mixture of 3 L of isopropanol and 3 L of n-heptane were introduced into a heatable stainless steel (RA4) pressure vessel having an internal sieve basket and a capacity of 20 L and the mixture was heated to 270° C. within 4 h, in the course of which the pressure in the pressure vessel was limited to 28 bar. This was followed by isothermal decompression within 60 min. The cooled reaction product was withdrawn and subjected to further drying at 80° C. and 200 mbar for about 2 h.

About 93% by weight of the resulting aerogel was in the form of granules having a particle size distribution of about 1 to 8 mm. The bulk density was 85 to 90 g/L. About 7% by weight of the product was in the form of fines (powder) having slightly elevated bulk density. The specific surface area was 370 $m^2/g$. The carbon content was 6% by weight.

Example 9

Isopropanol, N-hexane; Volume Ratio 5:95

500 g of the isopropanol-comprising silicon dioxide nanoparticle agglomerates from preparation example 6 were introduced together with 2 L of a mixture of isopropanol with n-hexane (volume ratio 5:95) into a heatable stainless steel (RA4) pressure vessel having an internal sieve basket and a capacity of 20 L. The reaction mixture was heated to 240° C. within 5 h, in the course of which the pressure was limited to 30 bar. Thereafter, the reaction mixture was decompressed isothermally within 90 min. The cooled product was withdrawn and dried at 70° C. and 0.2 bar for about 2 h.

Surface-modified silicon dioxide nanoparticle agglomerates were obtained with about the same dimensions as the unmodified silicon dioxide nanoparticle agglomerates. The bulk density of the agglomerates obtained was about 100 g/L. The specific surface area of the agglomerates was about 400 to 500 $m^2/g$. The carbon content of the agglomerates was about 2.5% by weight. The product formed was hydrophobic with a contact angle of about 120°.

The invention claimed is:

1. A process for producing porous or finely divided solid inorganic materials, the surface of which has been modified with at least one organic substance, comprising a treatment with an organic liquid under supercritical conditions, wherein the process comprises:
   a) providing a hydrogel of the inorganic material;
   b) removing the water by treating the hydrogel with an anhydrous organic liquid, and
   c) drying the treated hydrogel under supercritical conditions in the presence of the organic liquid;
   or
   a') providing a finely divided solid inorganic material having an unmodified surface and
   b') treating the material provided in step a') with the organic liquid under supercritical conditions;
   wherein the solid inorganic material is an aerogel; the organic liquid being a mixture of at least one reactive organic substance which can react with the atoms of the inorganic material to form a chemical bond and at least one inert organic substance and mixtures thereof, wherein the mixture has a critical point which is at lower temperature and/or lower pressure than the critical point of the reactive organic substance; wherein the inert organic substance is a C3-C8-alkane and the reactive organic substance is a C2-C4-alkanol.

2. The process according to claim 1, wherein removal of the water is preceded by freeing the hydrogel of ionic constituents by washing with water or dilute aqueous solutions of inorganic bases.

3. The process according to claim 1, wherein the water is removed by treating the hydrogel with the anhydrous organic liquid under subcritical conditions.

4. The process according to claim 1, wherein the finely divided solid inorganic material is a structure which, in at least one spatial direction, has a material thickness M of not more than 1000 nm, and as an overall structure has, in at least one spatial direction, a dimension which is at least 5 times the material thickness M.

5. The process according to claim 4, wherein the overall structure has, in at least one spatial direction, a dimension in the range from 10 μm to 10 cm.

6. The process according to claim 1, wherein the solid inorganic material is in the form of
   agglomerates of particles having a mean particle diameter of not more than 100 nm, the proportion by volume of the inorganic material, based on the total volume of the agglomerate, being in the range from 1 to 20% by volume.

7. The process according to claim 1, wherein the solid inorganic material is selected from metal oxides and semimetal oxides.

8. The process according to claim 7, wherein the solid inorganic material comprises, as the main component, at least one oxide selected from the group consisting of silicon dioxide, zinc oxide, tin(IV) oxide, titanium(IV) oxide and aluminum oxide in an amount of 90 to 100% by weight, based on the total weight of the solid inorganic material.

9. The process according to claim 1, wherein the inert organic substance has a lower critical temperature and/or a lower critical pressure than the reactive organic substance.

10. The process according to claim 1, wherein the inert organic substance has a critical temperature in the range from 20 to 300° C.

11. The process according to claim 1, wherein the inert organic substance has a critical pressure in the range from 20 to 80 bar.

12. The process according to claim 1, wherein the treatment with the organic liquid is effected at a temperature of not more than 40° C. above the critical temperature of the organic liquid.

13. The process according to claim 1, wherein the finely divided solid inorganic material is a structure which, in at least one spatial direction, has a material thickness M of 2 to 500 nm, and as an overall structure has, in at least one spatial direction, a dimension which is at least 5 times the material thickness M.

14. The process according to claim 1, wherein the solid inorganic material is in the form of
agglomerates of particles having a mean particle diameter of 2 to 80 nm, the proportion by volume of the inorganic material, based on the total volume of the agglomerate, being in the range from 1 to 20% by volume.

15. The process according to claim 1, wherein the inert organic substance is n-pentane, n-hexane or n-heptane, and the reactive organic substance is isopropanol.

* * * * *